United States Patent
Pressacco et al.

(10) Patent No.: US 11,259,931 B2
(45) Date of Patent: Mar. 1, 2022

(54) GLENOID ANCHOR FOR A SHOULDER JOINT PROSTHESIS

(71) Applicant: LIMACORPORATE S.P.A., Udine (IT)

(72) Inventors: Michele Pressacco, Udine (IT); Andrea Fattori, Udine (IT); Gabriele Vidoni, Udine (IT); Patrick Michael Connor, Charlotte, NC (US); Rolando Izquierdo, Crystal Lake, IL (US); Peter Channel Poon, Auckland (NZ); Jason J. Scalise, Phoenix, AZ (US)

(73) Assignee: LIMACORPORATE S.P.A., San Daniele del Friuli (IT)

( * ) Notice: Subject to any disclaimer, the term of this patent is extended or adjusted under 35 U.S.C. 154(b) by 532 days.

(21) Appl. No.: 15/558,543

(22) PCT Filed: Mar. 21, 2016

(86) PCT No.: PCT/IB2016/051574
§ 371 (c)(1),
(2) Date: Sep. 14, 2017

(87) PCT Pub. No.: WO2016/147163
PCT Pub. Date: Sep. 22, 2016

(65) Prior Publication Data
US 2018/0064537 A1    Mar. 8, 2018

(30) Foreign Application Priority Data
Mar. 19, 2015  (IT) .......................... MI2015A000417

(51) Int. Cl.
*A61F 2/30*    (2006.01)
*A61F 2/40*    (2006.01)

(52) U.S. Cl.
CPC ........ *A61F 2/30749* (2013.01); *A61F 2/4081* (2013.01); *A61F 2002/305* (2013.01);
(Continued)

(58) Field of Classification Search
CPC ................ A61F 2/30749; A61F 2/4081; A61F 2002/30332; A61F 2002/30349;
(Continued)

(56) References Cited

U.S. PATENT DOCUMENTS

| 6,406,495 B1 * | 6/2002 | Schoch ................. A61F 2/4081 623/19.11 |
| 2003/0004577 A1 * | 1/2003 | Running ............... A61F 2/3868 623/20.27 |

(Continued)

FOREIGN PATENT DOCUMENTS

| EP | 1787603 A1 | 5/2007 |
| FR | 2 977 791 A1 | 1/2013 |
| WO | WO 2011/098890 A1 | 8/2011 |

OTHER PUBLICATIONS

International Search Report in application No. PCT/IB2016/051574, dated Jul. 13, 2016, 4 pages.
(Continued)

*Primary Examiner* — Yashita Sharma
*Assistant Examiner* — Melissa A Hoban
(74) *Attorney, Agent, or Firm* — Hickman Becker Bingham Ledesma LLP; Malgorzata A. Kulczycka

(57) ABSTRACT

The present invention relates to an improved glenoid anchor for a shoulder joint prosthesis, in particular a convertible prosthesis, of the type intended to be fixed to the glenoid cavity of the shoulder blade and comprising: —a pin (2) with an internally hollow and essentially thimble-like conical sleeve (12), which has a tapered distal end (3) and an open proximal end (4); —an annular recess (15) formed inside the
(Continued)

cavity (13) of the pin (2) in the vicinity of said open proximal end (4), for receiving by means of snap-engagement an edge (34) of a lug (30) of a prosthesis component (9); —at least one pair of oppositely arranged anti-rotation notches (16, 17) in the proximity of said annular groove (15) for receiving by means of snap fit oppositely arranged teeth (18, 19) of the same lug (30) intended to be snap-engaged together with said pin (2).

16 Claims, 15 Drawing Sheets

(52) U.S. Cl.
CPC ............... *A61F 2002/30332* (2013.01); *A61F 2002/30336* (2013.01); *A61F 2002/30349* (2013.01); *A61F 2002/30367* (2013.01); *A61F 2002/30507* (2013.01); *A61F 2002/30878* (2013.01); *A61F 2002/4085* (2013.01)

(58) Field of Classification Search
CPC ...... A61F 2002/30367; A61F 2002/305; A61F 2002/30507; A61F 2002/30878; A61F 2002/4085; A61F 2002/30336

See application file for complete search history.

(56) References Cited

U.S. PATENT DOCUMENTS

| 2007/0219638 | A1* | 9/2007 | Jones | A61F 2/4081 |
| --- | --- | --- | --- | --- |
| | | | | 623/19.11 |
| 2008/0294268 | A1* | 11/2008 | Baum | A61F 2/4081 |
| | | | | 623/23.42 |
| 2012/0221111 | A1* | 8/2012 | Burkhead, Jr. | A61F 2/4081 |
| | | | | 623/19.11 |
| 2013/0150972 | A1* | 6/2013 | Iannotti | A61F 2/4081 |
| | | | | 623/18.11 |
| 2014/0194995 | A1 | 7/2014 | Koka | |

OTHER PUBLICATIONS

International Preliminary Examining Authority, "Search Report" in application No. PCT/IB2016/051574, dated Jul. 7, 2017, 14 pages.

* cited by examiner

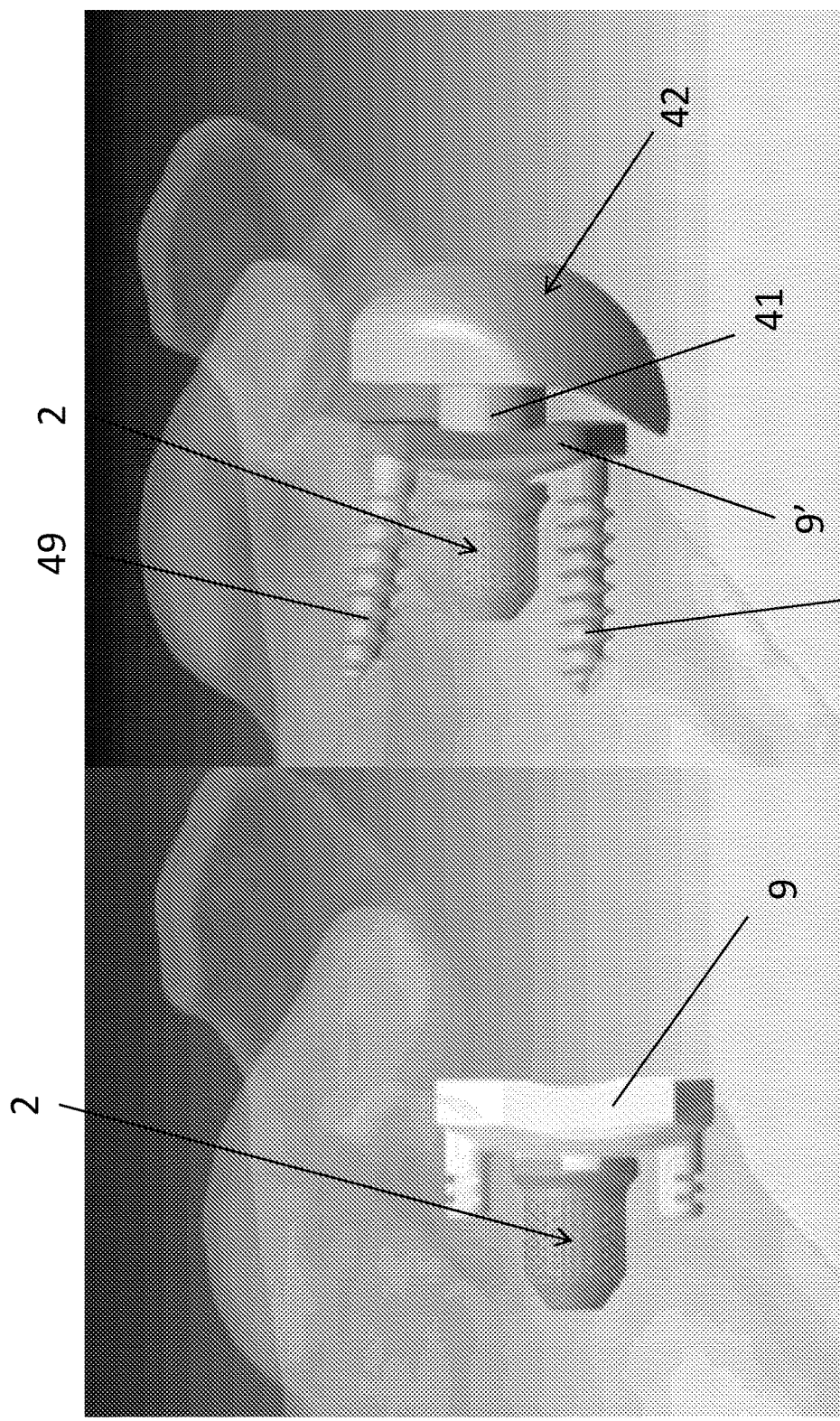

GLENOID ANCHOR FOR A SHOULDER JOINT PROSTHESIS

This application is a US national stage application filed under 35 U.S.C. § 371 based upon International Patent Application PCT/IB2016/051574, filed 21 Mar. 2016, which claims the benefit of Italian application MI2015A000417, filed 19 Mar. 2015, the entire contents of which are hereby incorporated by reference as if fully set forth herein for all purposes.

FIELD OF APPLICATION

The present invention relates to an improved glenoid anchor for a prosthesis of the shoulder joint, in particular a hybrid prosthesis, namely a convertible prosthesis.

The invention relates more specifically, but not exclusively, to an accessory anchor element which allows stable and secure fixing of prosthesis for articulation of the shoulder with the glenoid cavity of the shoulder blade and conversion of this prosthesis from an anatomical prosthesis to a reverse prosthesis; the description which follows is provided with reference to this specific field of application in order to simplify description thereof.

PRIOR ART

As is well-known, shoulder prostheses which reproduce in a more or less natural manner the glenohumeral anatomy are regularly used. These prostheses are defined as being anatomical and comprise an anchor element or glenoid insert which is fixed to the shoulder blade, inside the glenoid cavity.

The prostheses have a glenoid and a humeral prosthesis component. The insert in question allows the mounting of a concave glenoid component which is articulated with a spherical component which represents the humeral component of the prosthesis and is fixed to the top of the humerus by means of a fixing stem inserted inside the humerus itself.

Shoulder prostheses which reproduce in a reverse manner the glenohumeral anatomy are known too; these prostheses are defined as being reverse.

In reverse prostheses the form of the artificial articulation is substantially reversed with respect to anatomical prostheses. In them in fact the glenoid component has one end with a convex articular surface which is rotatably engaged with a cup of a concave articular surface rigidly fixed to the humerus.

For some years this technique has proved to be the most effective technique for best resolving critical situations of instability of the rotator cuff and therefore the joint.

A reverse prosthesis of known type is described for example in European patent No. 1 656 910 B1 in the name of the Applicant. This patent describes a reverse prosthesis of the shoulder having a convex articulation element 25 associated with the glenoid cavity; there is an annular metal element 24 which is fixed to the articulation element 25 and which acts as an intermediate element for connection to an anchor element 18 inserted inside the glenoid cavity and formed as one piece with a flange 16.

A similar anchor element of known type, intended for a reverse prosthesis, is described for example in European patent No. EP 1 598 034 B1 in the name of Zimmer and shown in FIG. 1. This patent describes an anchor element 10 comprising a conical pin portion 4 with peripheral ribs 20 and a flange 1 formed as one piece with a slightly concave shape. The flange has holes 3 and 21 so that it may be fastened to the glenoid cavity by means of screws.

Other examples of known technical solutions in which an anchor element with flange is used to mount the glenoid component of a reverse prosthesis are described in patent applications Nos. FR 2 869 217 and EP 1 782 764. However, these solutions are intended for implantology without the use of cement, in which solutions the anchoring component is always formed in one piece with the flange that allows the fixing by means of screws of the prosthesis component into the glenoid cavity.

There are also other solutions which propose the use of a porous titanium anchor element with a more or less shaped—for example lobe-like—form which requires however the definition of a corresponding receiving seat to be formed in the glenoid cavity.

Although advantageous in many respects and substantially fulfilling their purpose, all these known solutions have a common drawback consisting in the fact they are not always able to ensure correct and durable fixing of the anchor element inside the glenoid cavity, with obvious serious risks of slackening and/or separation.

In particular, the presence of the flange formed as one piece with the pin portion of the anchor element is a limitation for the surgeon who must correctly form in the glenoid cavity the seat for the pin portion, making sure, however, to position it so that the flange may adhere with a form-fit to the surface of the glenoid cavity.

Moreover, the form of these anchor elements does not facilitate multi-functional use thereof, in the sense that it does not allow them to be used equally well for an anatomical prosthesis and for a reverse prosthesis.

A known technical solution proposed by the same Applicant and described in European patent No. EP 1 472 999 B1 envisages an anchoring element, called a Metal back, provided with a concave flange which allows switch-over from the anatomical prosthesis to reverse prosthesis without necessarily having to remove the anchor element.

Although advantageous from various points of view and substantially fulfilling its purpose, this solution also has a drawback in that the flange has, affixed thereon, a bearing of synthetic material, normally polyethylene, which must in any case be removed during conversion of the prosthesis, so that it may be replaced by another component with a convex form. Moreover, in the case of wear of the bearing of synthetic material there will be metal-to-metal contact between the humeral head and the glenoid flange.

The object of the invention is to provide an improved glenoid anchor for a hybrid prosthesis of the shoulder joint which has structural and functional characteristics such as to overcome the drawbacks mentioned with reference to the prior art and allow an easy conversion from an anatomical prosthesis to a reverse prosthesis, even during the surgical phase of implantation of this prosthesis, without having to remove the pin integrated in the bone.

SUMMARY OF THE INVENTION

The proposed solution forming the basis of the present invention is that of providing an anchor element in which the pin portion of this element is structurally independent of the flange portion which takes the form of a shield or in any case a bearing-type prosthesis component which can be snap-engaged together with the pin portion. Advantageously, engagement between the prosthesis component and the pin portion is performed by means of mechanical interference.

On the basis of this proposed solution, a first embodiment of the anchor element according to the invention comprises:

- an internally hollow and essentially thimble-like pin with a conical sleeve, which has a tapered distal end and an open proximal end;
- an annular recess formed inside the cavity of the pin in the vicinity of said open proximal end, for receiving by means of snap-engagement an edge of a lug of a prosthesis component;
- at least one pair of oppositely arranged anti-rotation notches in the proximity of said annular groove for receiving oppositely arranged teeth of the same prosthesis component intended to be snap-engaged together with said pin.

Essentially, with the solution according to the present invention it is envisaged that the pin portion of the anchor element is designed separately from the associated flange, which is instead formed integrally in the solutions of the prior art, and is provided with quick-fit coupling means for snap-engaging an interface bearing. This bearing forms a kind of interface flange which may be easily removed in order to convert the anatomical prosthesis to a reverse prosthesis without removing the pin from the glenoid cavity.

A conical coupling with controlled mechanical interference between a conical lug of the bearing flange or an articular insert of the prosthesis component and the internal cavity of the pin is envisaged. The degree of penetration is determined by lateral lugs of the flange or the insert which ensure also maximum supporting of the pin at the maximum flexing point.

Also envisaged inside the cavity are anti-rotation notches which are designed to receive corresponding teeth arranged with regular spacing on the base of said conical lug.

The assembly consisting of anchor element, bearing and humeral and glenoid components form a parts kit for the installation of a convertible hybrid prosthesis which may be mounted as an anatomical prosthesis or, if already mounted as an anatomical prosthesis, may be converted into a reverse prosthesis depending on the operating needs arising at the time.

BRIEF DESCRIPTION OF THE DRAWINGS

FIGS. 13 and 14 show photographic-like illustrations of the anchor and the prosthesis components according to the invention during use.

DETAILED DESCRIPTION

Figure 1:
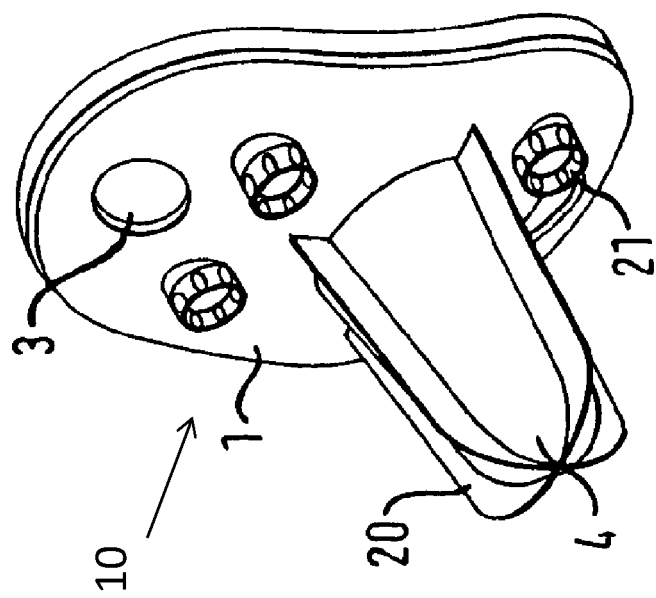
FIG. 1 shows a perspective view of an anchor for an artificial shoulder prosthesis designed in accordance with the prior art.
Figure 2:
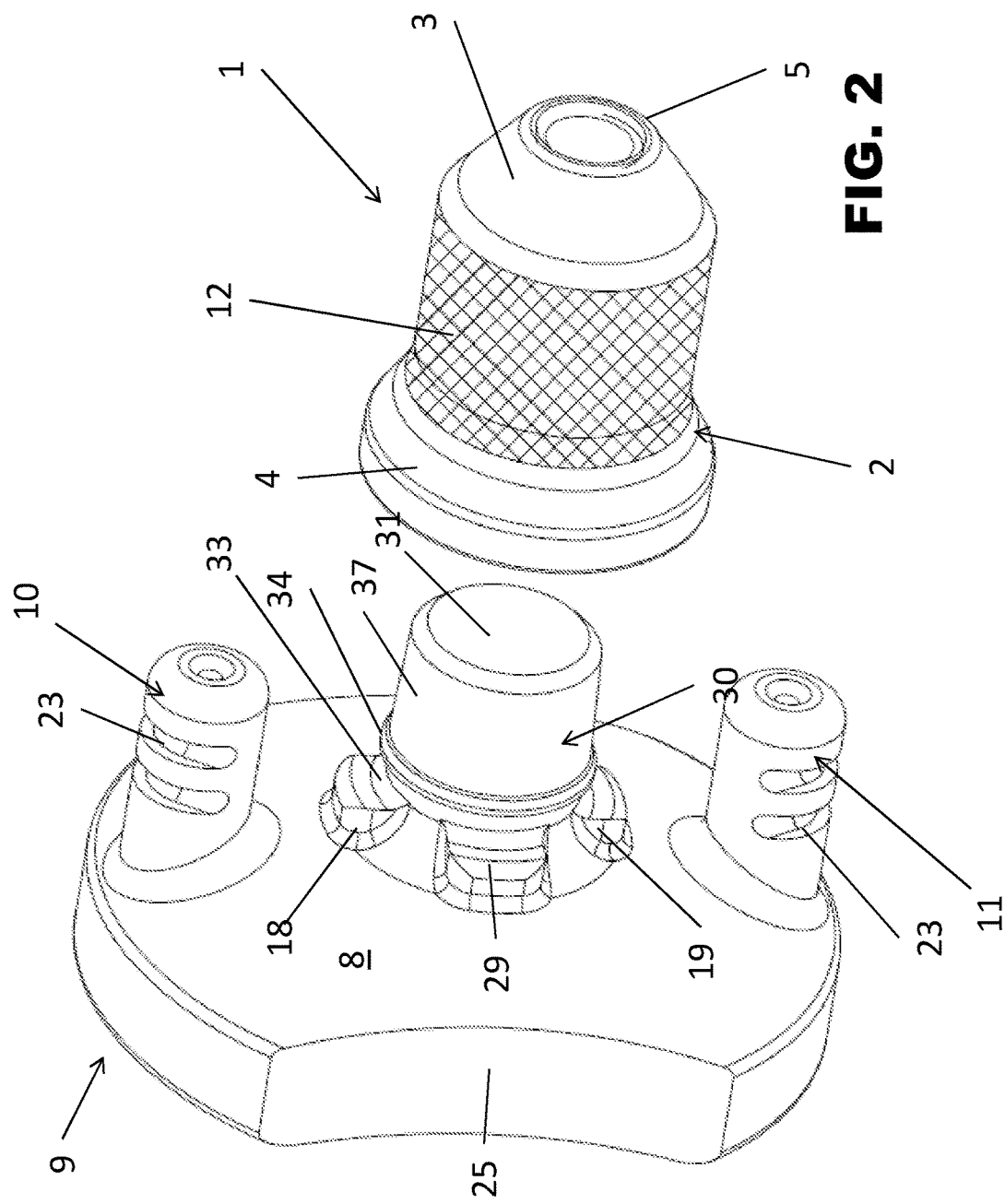
FIG. 2 shows a schematic perspective view of an anchor for an artificial shoulder prosthesis designed in accordance with the present invention.
Figure 3:
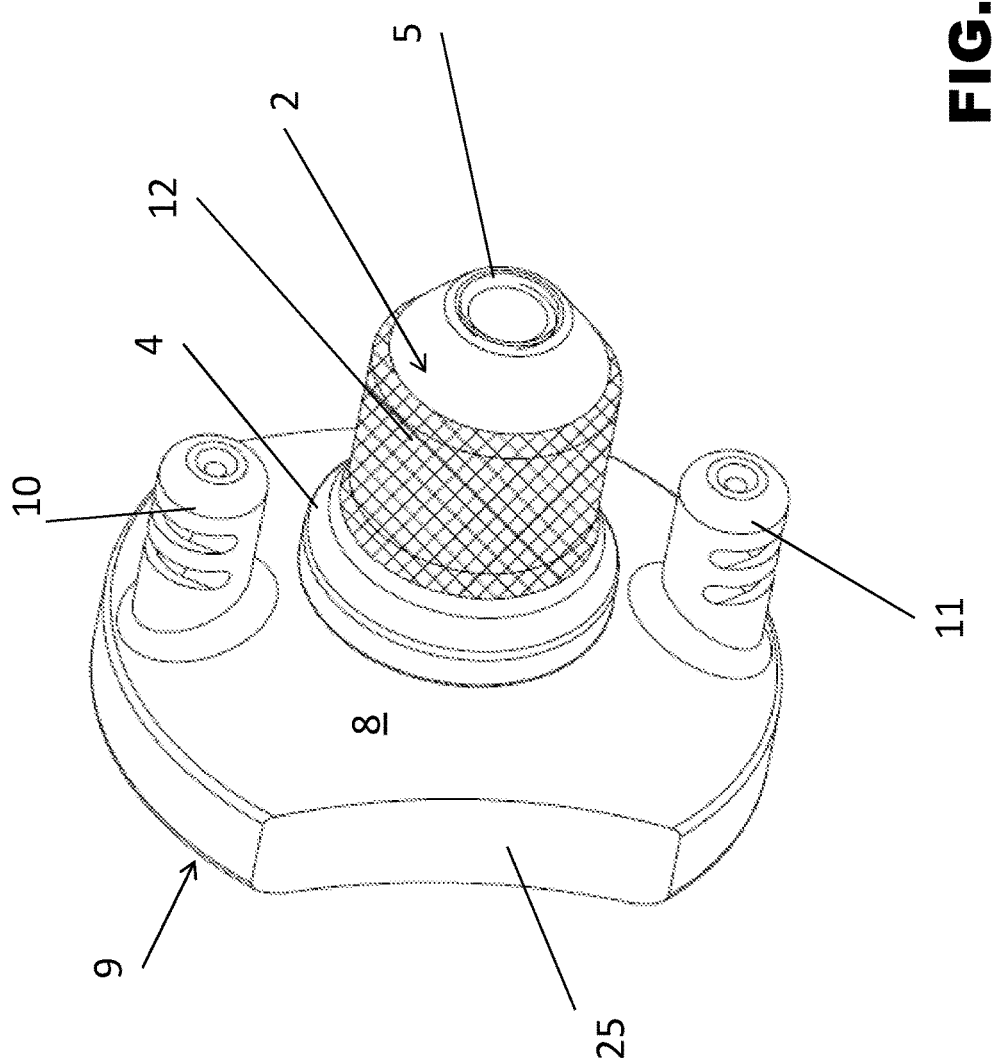
FIG. 3 shows a schematic perspective view of a prosthesis component cooperating with the anchor according to FIG. 2.
Figure 4:
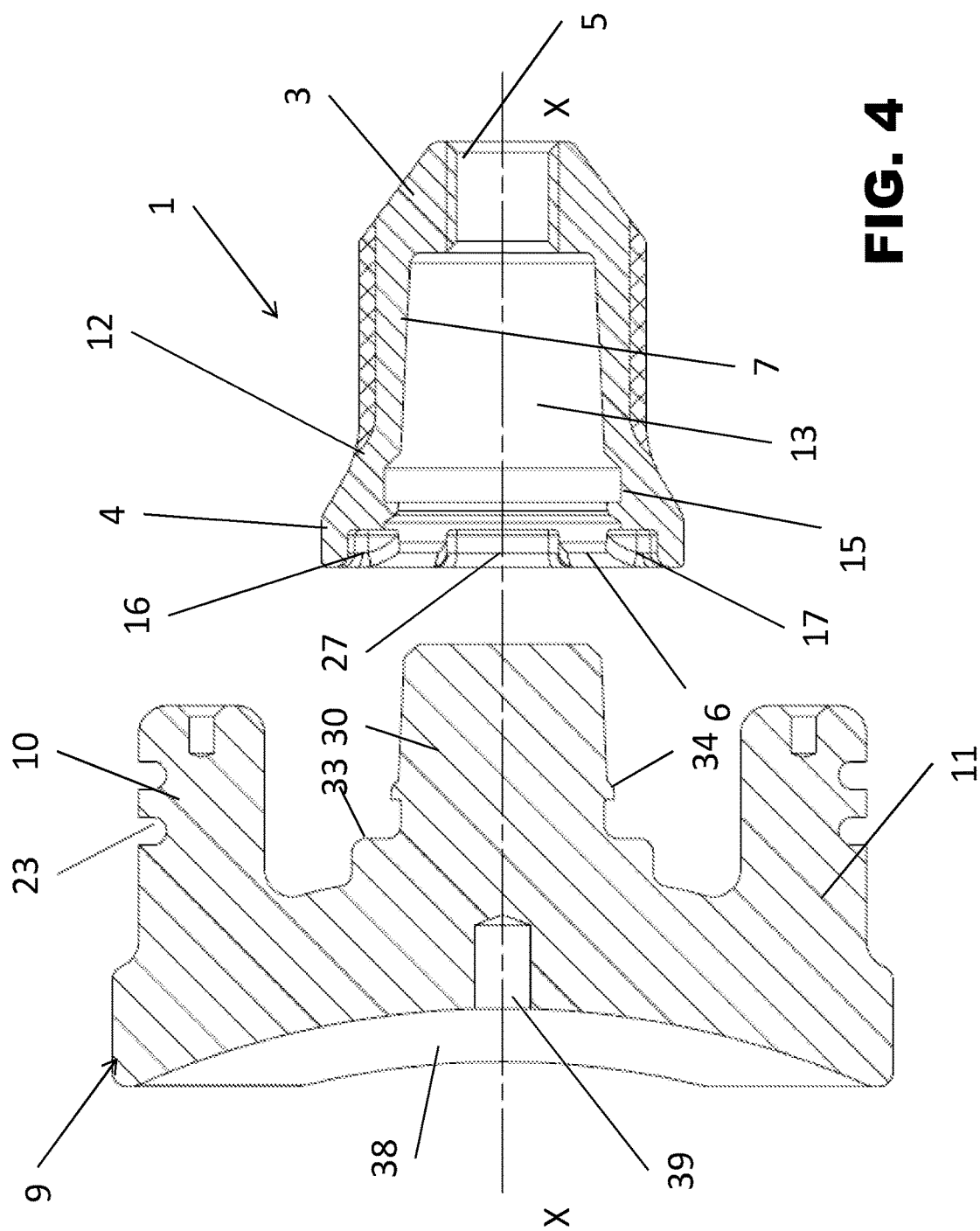
FIG. 4 shows a schematic longitudinally sectioned view of the anchor and the prosthesis component according to the invention during engagement with each other.

With reference to these figures, and in particular to the example shown in FIG. 2, 1 denotes overall and in schematic form an improved anchor element designed in accordance with the present invention for stably and securely fixing a prosthesis for the shoulder joint to the glenoid cavity of the shoulder blade.

In the description below reference will be made to this anchor element 1 using the simpler term "glenoid anchor".

Advantageously the anchor 1 is a component which allows the conversion of a shoulder joint prosthesis from an anatomical prosthesis to a reverse prosthesis. This anchor 1 is intended to cooperate with another, structurally independent, prosthesis component 9, which can be snap-engaged by means of a mechanical interference fit with the anchor 1 and which will be described in greater detail below.

The anchor 1 is intended to be surgically implanted in the glenoid cavity of the shoulder blade and has the function of supporting the loads and of being biologically integrated as a result of its generally rough finish.

The anchor 1 is substantially in the form of a pin 2 which is structurally independent of prosthesis component 9 and has an internally hollow conical sleeve 12 with an essentially thimble-likestructure. The pin 2 extends along a longitudinal axis X-X with a longitudinal dimension which is larger than its diameter or its radial volume. The pin 2 is made of a biocompatible metallic material, for example titanium or an alloy thereof, and has a generally rough finish, for example as described in the patent U.S. Ser. No. 12/601,510.

The outer surface of the sleeve 12 has an irregular or trabecular structure for favouring osteogenesis and bone integration and has been chosen so as to increase the associated contact friction of the pin 2 inside the corresponding receiving seat (not shown in the drawings) which the surgeon must prepare beforehand in the bone of the glenoid cavity of the shoulder blade.

The pin 2 has a tapered distal end 3 with an open hole 5 and an opposite flared proximal end 4. The hole 5 is correspondingly threaded so as to be engaged by means of screwing of a screw 45 for fixing the shoulder blade component of the prosthesis when it has a convex articular surface, as shown in FIG. 14.

As mentioned, the pin 2 is internally hollow and the proximal end 4 defines a proximal opening 6 which provides access to the conical internal cavity 13 of the pin 2.

A narrower diameter is provided adjacent to the proximal opening 6, but already inside the cavity 13 of the pin 2, said narrower diameter defining an internal step or edge 14 for seating, in bearing contact, a surface 33 of said prosthesis component 9 cooperating with the pin 2, which will be described below.

The internal cavity 13 of the pin 2 has, formed inside it, an annular recess 15 situated in the vicinity of the edge 14 in a predefined spaced relationship with respect thereto, towards the inside of the cavity 13.

Figure 5:
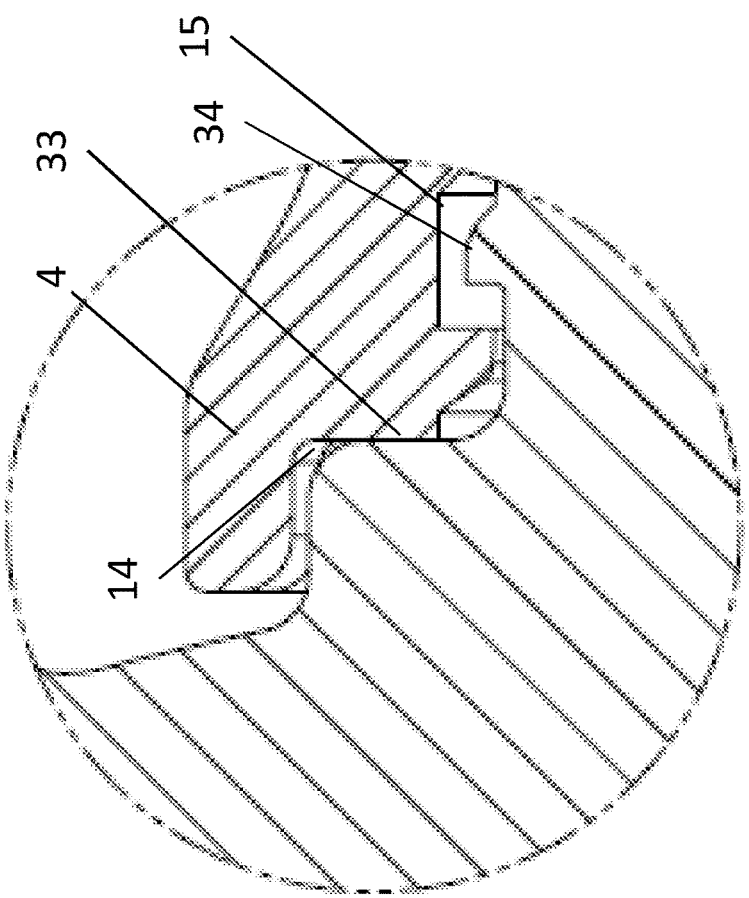
FIG. 5 shows a schematic sectioned view on a larger scale of a detail of the engagement between the anchor and the prosthesis component according to the present invention.

This annular recess 15 is intended to receive an annular edge 34 formed on a lug 30 of the prosthesis component 9 which is snap-engaged together with the anchor 1. As can be clearly seen in FIG. 5, the annular edge 34 of the prosthesis component 9 has a toothed profile which favours snap-engagement thereof after passing over the edge of the recess 15 and prevents removal of the component. Moreover, the degree of penetration of the insert of the prosthesis component 9 is determined by the surface 33 making bearing contact against the edge 14.

Figure 15:
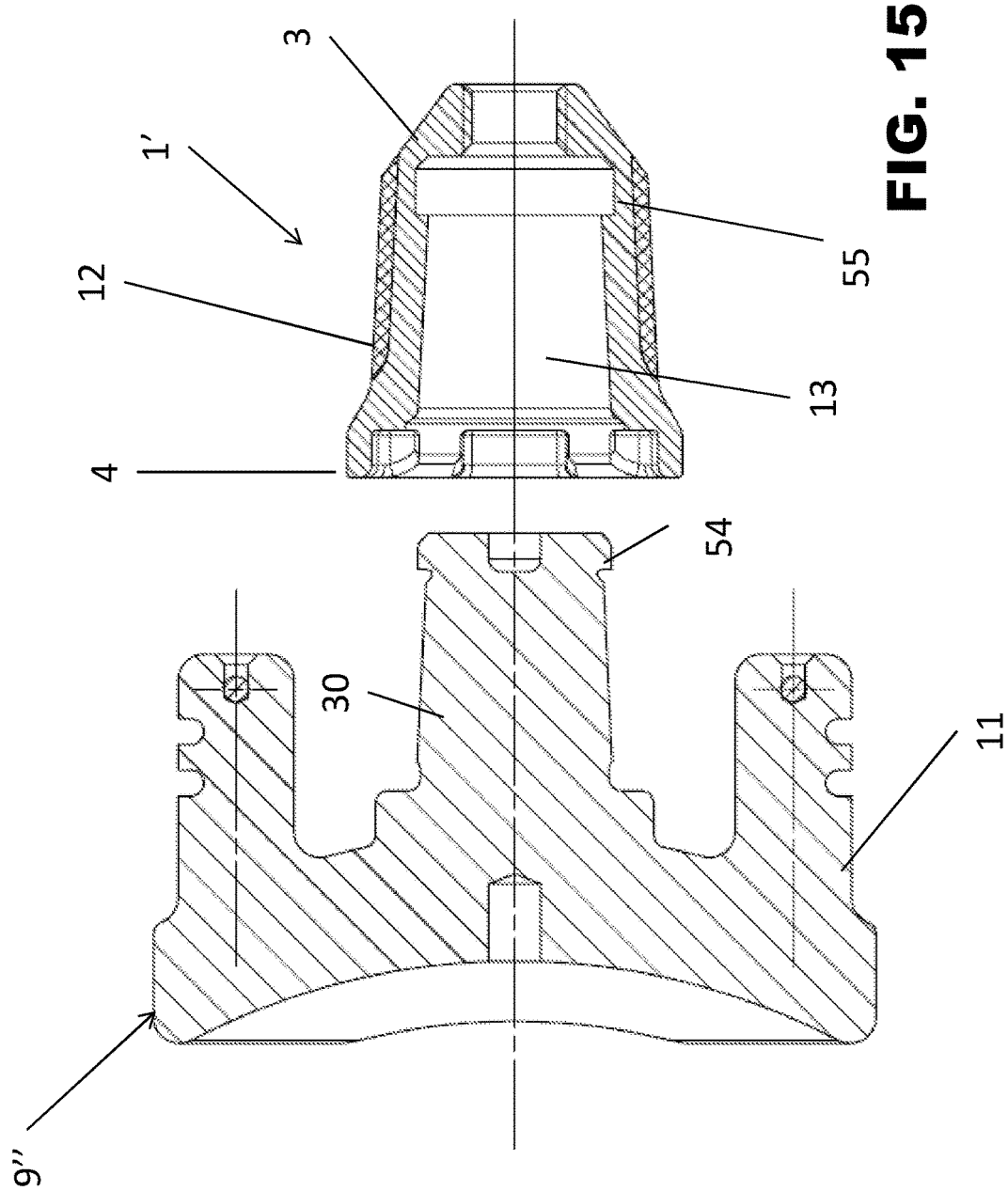
FIG. 15 shows a schematic longitudinally sectioned view of a second embodiment of the anchor and the prosthetic component according to the invention during engagement with each other.

In an another embodiment illustrated in FIG. 15, an annular recess 55 is formed in the internal cavity 13 of the pin 2, in the vicinity of the distal end 3.

Figure 16:
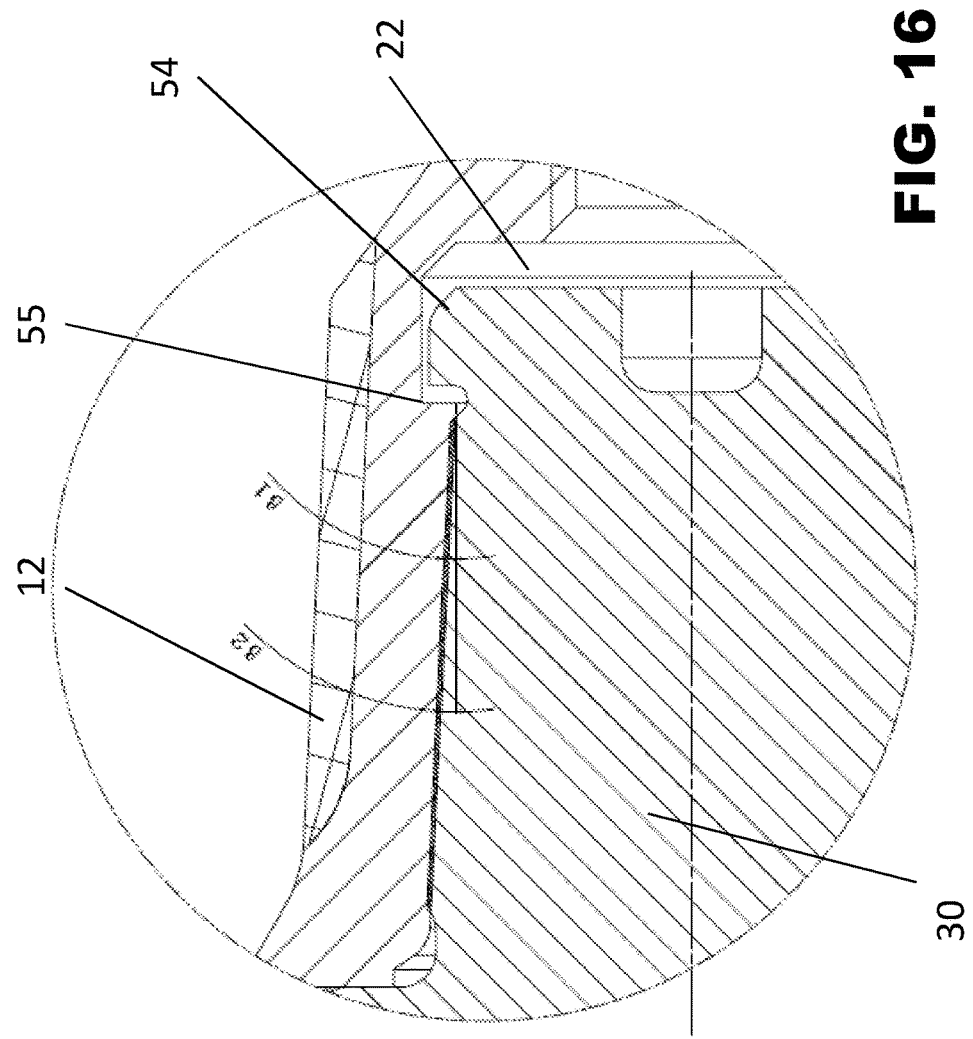
FIG. 16 shows a schematic sectional view on a larger scale of a detail of the engagement between the anchor and the prosthesis component of FIG. 15.

This annular recess 55 is intended to receive an annular edge 54 formed on a lug 30 of a prosthesis component 9" which is snap-engaged together with the anchor 1'. As can be clearly seen in FIG. 16, the annular edge 54 of the prosthesis component 9" has a toothed profile which favours snap-engagement thereof after passing over the edge of the recess 55 and prevents removal of said component. Moreover, the degree of penetration of the insert of the prosthesis component 9" is determined by the surface 33 making bearing contact against the edge 14.

In the region of the edge 14 and before the annular recess 15, in a proximal to distal direction, at least one pair of oppositely arranged anti-rotation notches 16, 17 are provided for receiving a corresponding tooth 18, 19 again of the same prosthesis component 9 which is intended to be snap-engaged with mechanical interference together with said pin 2.

Figure 7:
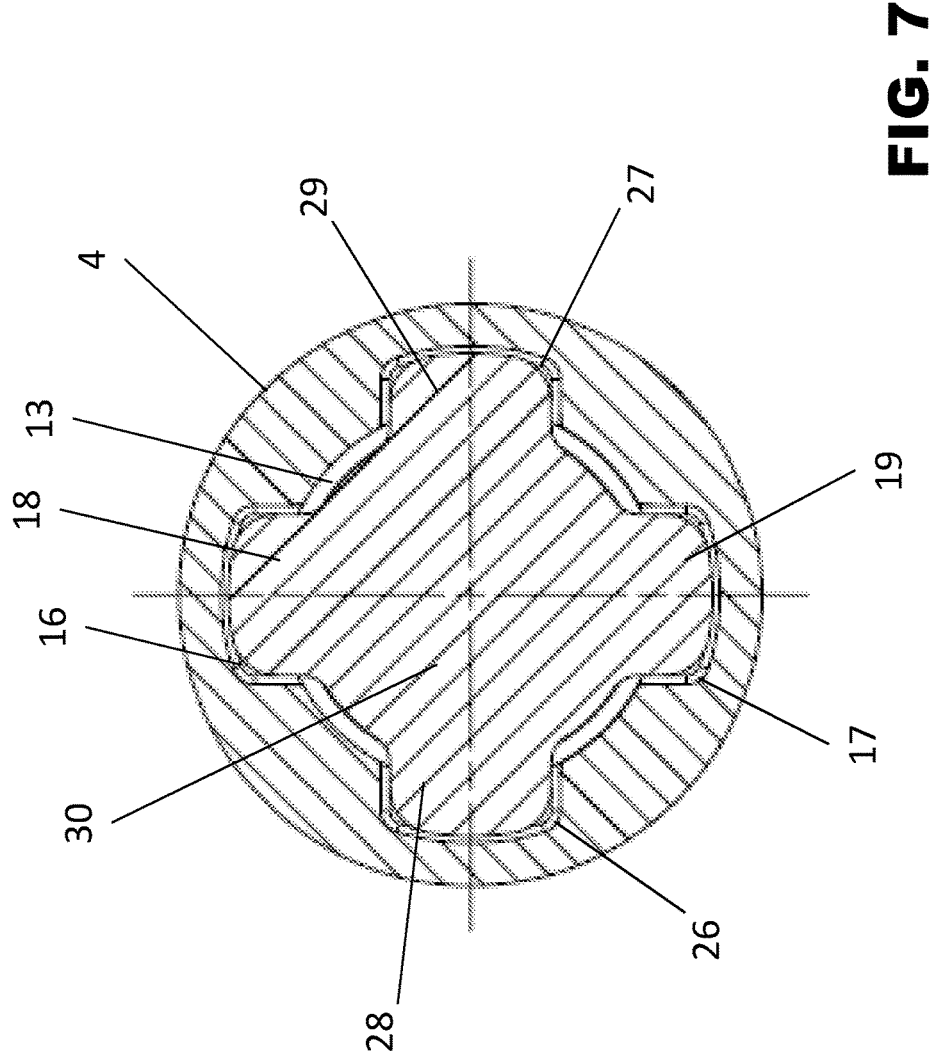
FIG. 7 shows a cross-sectional view along the line A-A of FIG. 6.
Figure 8:
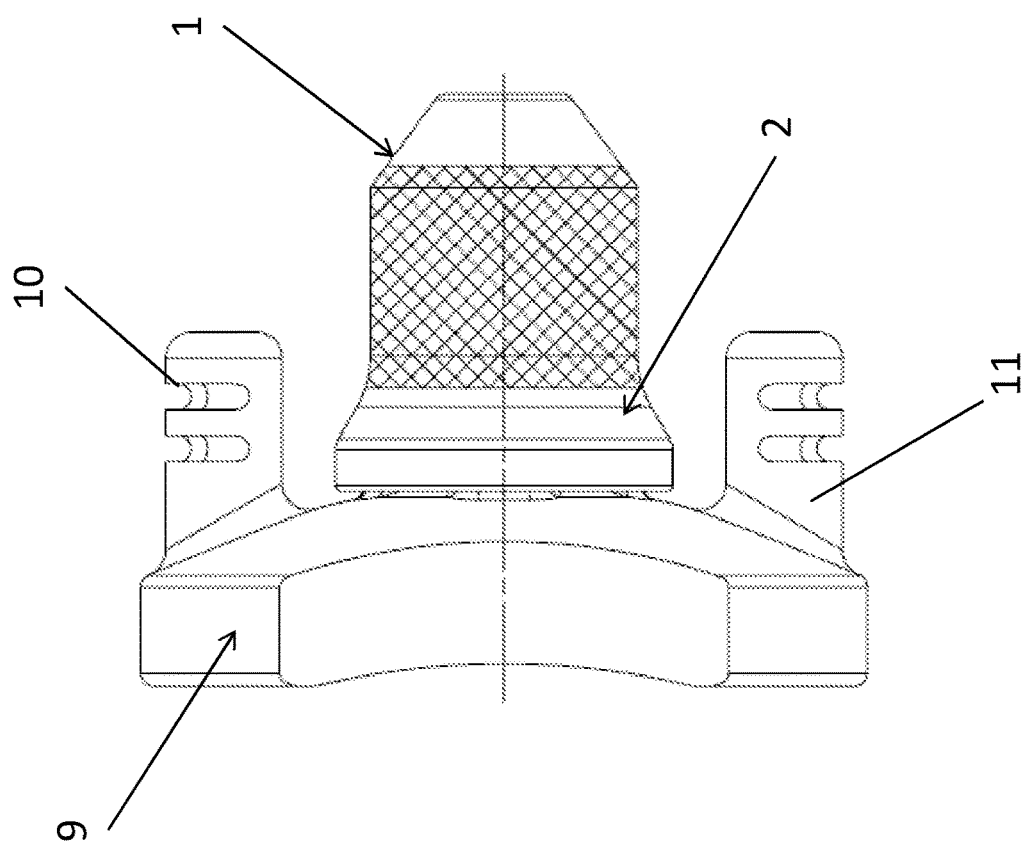
FIG. 8 shows a schematic lateral longitudinal view of the anchor and the prosthesis component according to the invention engaged with each other.

More particularly and preferably, four anti-rotation notches 16, 17, 26, 27 are provided, these being angularly spaced at 90° from each other and being intended to receive respectively and snap-engage with a corresponding tooth 18, 19, 28, 29 of said prosthesis component, as clearly shown in the cross-section of FIG. 7. These notches are also provided in anchor 1', which is intended to be engaged together with the prosthesis component 9".

Obviously it is quite possible to provide a greater number of notches and corresponding engaging teeth or for their relative arrangement to be chosen with a different angular spacing, without this resulting in any limitation of the Applicant's rights.

There now follows a detailed description of the structure of the prosthesis component 9 or 9" cooperating with the anchor 1. This component is preferably made of a biocompatible synthetic plastic material, for example a polyethylene with a high molecular weight (UHMWPE), soft enough to be pierced by fixing screws.

As already mentioned, the prosthesis component 9 has, in an anatomical prosthesis, the structure of a bearing which can be snap-engaged with controlled mechanical interference inside the pin portion 2 of the anchor 1.

As clearly shown in FIG. 2, the component 9 is formed with an essentially plate-like portion 8 which may also be defined as being a concave shield again in the case where it forms part of an anatomical prosthesis. This portion 8 has, extending therefrom, three lugs, i.e. a central lug 30 and two lugs on either side thereof, identified by the numbers 10 and 11.

The portion 8 has a slightly concave proximal surface 38 provided centrally with a cylindrical seat 39 which acts as a guide for inserting the centring wire for the instruments for removing the insert.

One side 25 of the portion 8 has a curved profile for anatomical reasons of ensuring better engagement with the glenoid cavity.

The three lugs 30, 10 and 11 extend the same direction and substantially with respective axes parallel to each other. It is also possible, however, for the axes of the lateral lugs 10, 11 to be more than three in number, for example arranged at 120° and therefore not in the same plane.

The central lug 30 has a conical form with a free end 31 and is intended to be inserted with a form-fit inside the internal cavity 13 of the pin 2. This lug 30 has a longitudinal axis which coincides substantially with the axis X-X of the pin 2 when the two components 1 and 9 are engaged with each other.

An annular edge 34 is formed on the outer surface 37 of the lug 30 in the vicinity of its generating base, as clearly shown in FIG. 2.

More precisely, the base of the lug 30 is provided with teeth 18, 19, 28, 29 which are intended to engage with the notches 16, 17, 26, 27. The aforementioned teeth are also clearly shown in FIG. 2.

The end surface 33 of each of the teeth 18, 19, 28, 29 is substantially flat and parallel to the surface of the free end 31 of the lug 30, substantially perpendicular to its axis.

Figure 9:
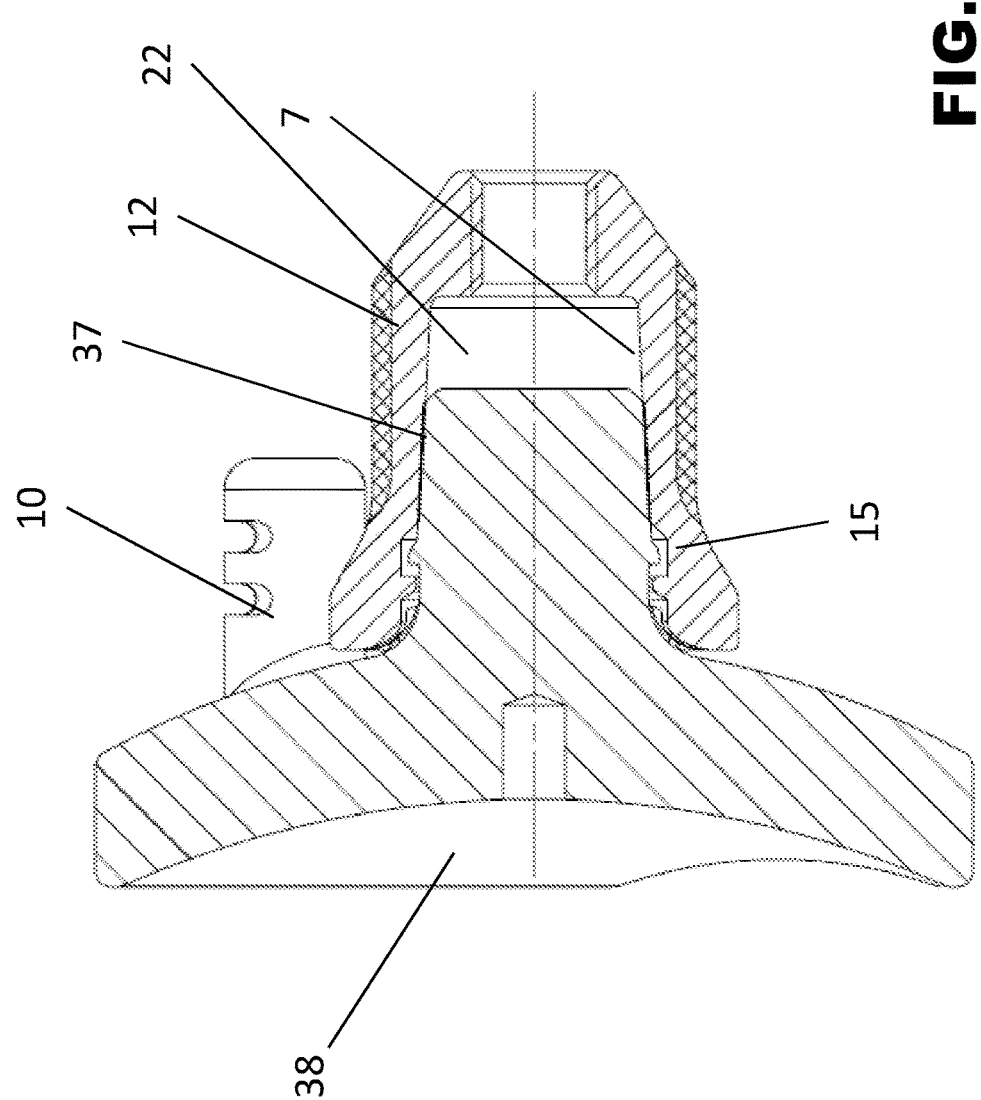
FIG. 9 shows a further, schematic, partially longitudinally sectioned view of the anchor and the prosthesis component according to the invention engaged with each other.
Figure 10:
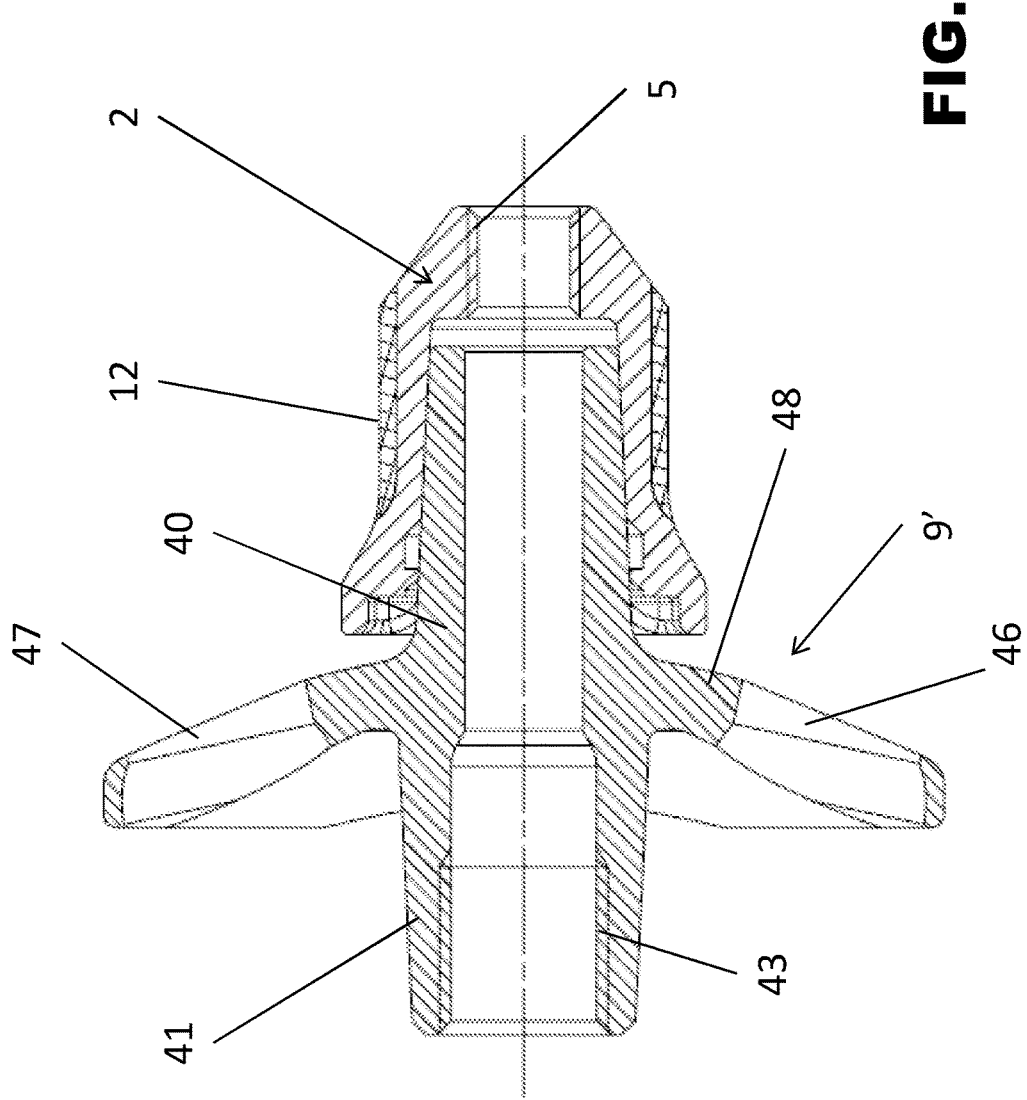
FIG. 10 shows a schematic longitudinally sectioned view of the anchor and another prosthesis component according to the invention engaged with each other.
Figure 11:
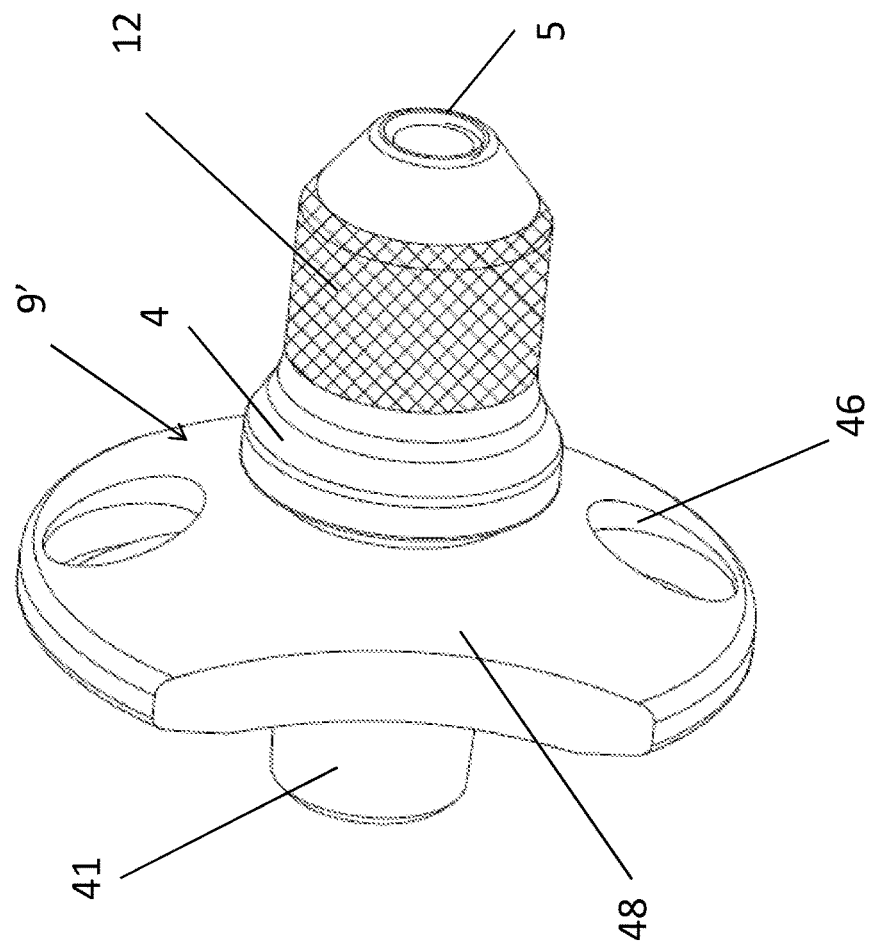
FIG. 11 shows a perspective view of the anchor and the other prosthesis component according to the invention—in particular a component which allows conversion of the prosthesis from the anatomical version to reverse version—engaged with each other.

Advantageously, according to the present invention, the surface 7 of the internal cavity 13 of the pin 2 is inclined with respect to the longitudinal axis X-X of said pin at an angle $\beta$ with a substantial reduction of the internal diameter towards the distal end 3 of the pin 2, as shown in FIG. 9.

Similarly, the outer surface 37 of the central lug 30 of the component 9 is inclined with respect to the longitudinal axis of this lug 30, which coincides substantially with the axis X-X when the two components 1 and 9 are engaged with each other. Essentially the outer surface 37 is inclined with respect to the axis X-X at angle other than $\beta$ and such that the mechanical interference will be variable along the axis of the pin 2.

Figure 6:
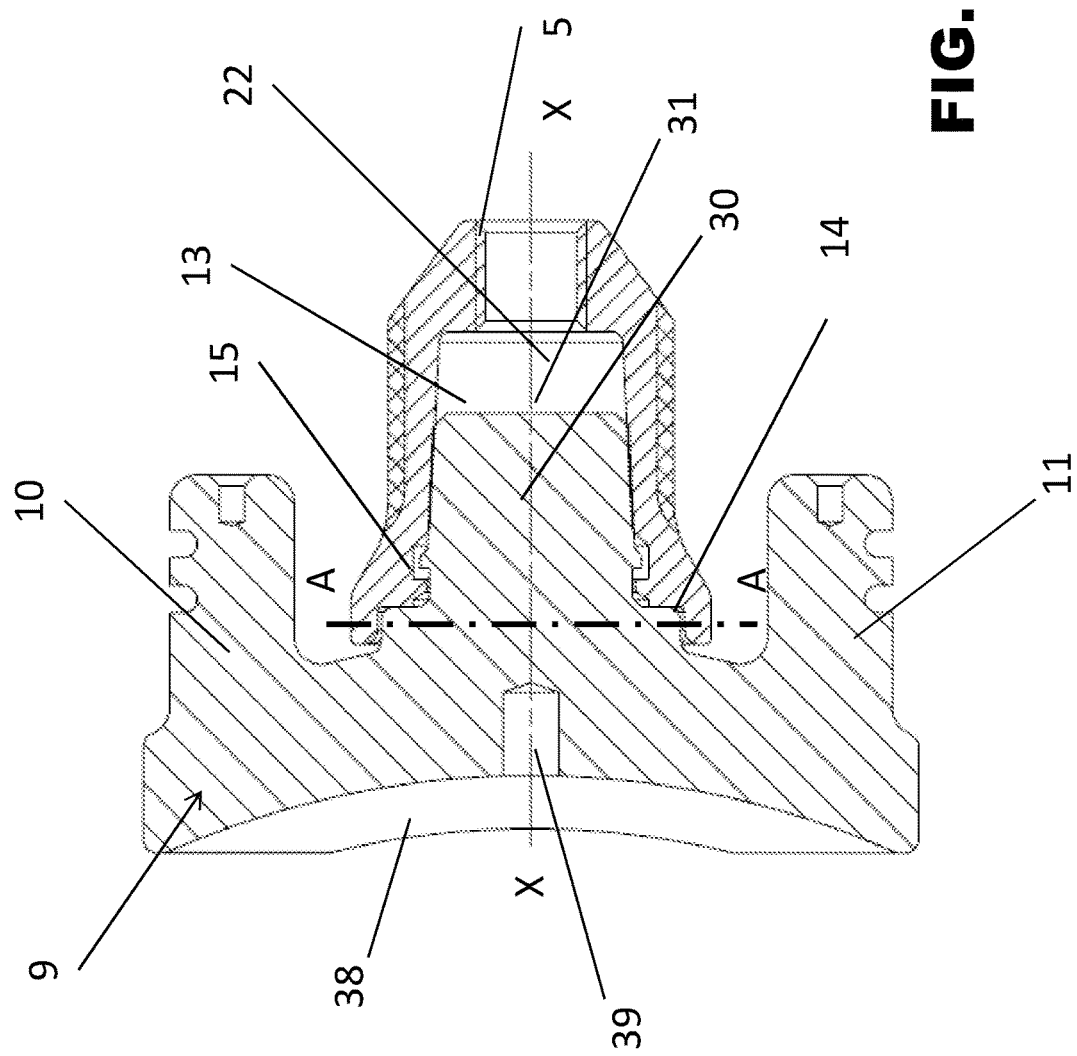
FIG. 6 shows a schematic longitudinally sectioned view of the anchor and the prosthesis component according to the invention engaged with each other.

This means that when the lug 30 of the prosthesis component 9 is inserted inside the internal cavity 13 of the pin 2, it penetrates until it causes an interference between the two surfaces 7 and 37 owing to the different diameters, substantially locking the lug 30 inside the cavity 13 when said lug has nearly reached the bottom of the cavity 13, as clearly shown in FIG. 6. The difference between the angles of the inclinations determines the variability of the interference along the axis X-X.

The projection of the lug 30 and the choice of the surface inclinations defined by the angles $\beta$ and $\delta$, with $\delta$ of the lug slightly smaller than $\beta$ of the cavity, is designed so as to obtain a desired gap 22 in the vicinity of the part of the cavity 13 close to the distal opening 5 of the pin 2. In other words, the geometric dimensions of the lug 30 and the cavity 13 are chosen so as to ensure that the end surface 31 of the lug 30 remains at a predefined distance from the distal end of the cavity 13. When the engagement with controlled interference between the lug 30 and the cavity 13 is obtained, at the same time snap-engagement of the annular edge 34 inside the corresponding recess 15 occurs.

Similarly, owing to the relative geometric dimensions, engagement also occurs between the teeth 18, 19, 28 and 29 at the base of the lug 30 which come into bearing contact with the respective notches 16, 17, 26, 27 formed in the vicinity of the mouth 6 of the cavity 13.

In this way bearing contact between the end surface 33 of the teeth 18, 19, 28 and 29 and the internal edge 14 is obtained. This bearing contact completes the engagement between the component 9 and the anchor 1 and forms a kind of end-of-travel stop for the penetration of the lug 30 inside the cavity 13.

Even in the embodiment of FIG. 15, in which a distal engagement between the annular recess 55 of the pin 2 and the edge 54 of the lug 30 of the component 9" is provided, an interference between the internal surface of the cavity 13 and the outer surface 37 of the lug 30 still occurs.

In this case, the prosthesis component 9" is inserted into the internal cavity 13 of the pin 2 and penetrates until an interference between the two surfaces 7 and 37 is caused, owing to the different diameters, substantially locking the lug 30 inside the cavity 13 when the edge 54 is snap-engaged into the recess 55. The projection of the lug 30 and the selection of the surface inclinations defined by the angles β1 and β2, with β2 of the lug being slightly smaller than β1 of the cavity, is accurately designed so as to obtain a desired gap 22 in the vicinity of the part of the cavity 13 which is close to the distal opening 5 of the pin 2, as clearly shown in FIG. 16.

It should also be pointed out that the other two lugs 10, 11 parallel to the central lug 30 are pins which are made of the same material as the prosthesis component and which are inserted inside corresponding holes formed in the bottom of the glenoid seat and which serve for support and functional stability. In an alternative embodiment shown partially in FIG. 9 at least three lugs or pins distributed at 120° around the central lug 30 are provided.

From the above description it clearly emerges that the anchor according to the present invention achieves the designated objects and offers numerous advantages, the main ones of which will be listed hereinbelow.

Essentially, with the solution according to the present invention it is envisaged that the pin portion 2 of the anchor element 1 is designed separately from the associated flange, which is instead formed integrally in the solutions of the prior art, and is provided with quick-fit coupling means 7, 15, 14 for snap-engaging the prosthesis component in the form of an interface bearing 9 or 9".

This bearing 9, 9" forms a kind of flange which may be easily removed in order to convert the anatomical prosthesis to a reverse prosthesis without removing the pin 2.

Figure 12:
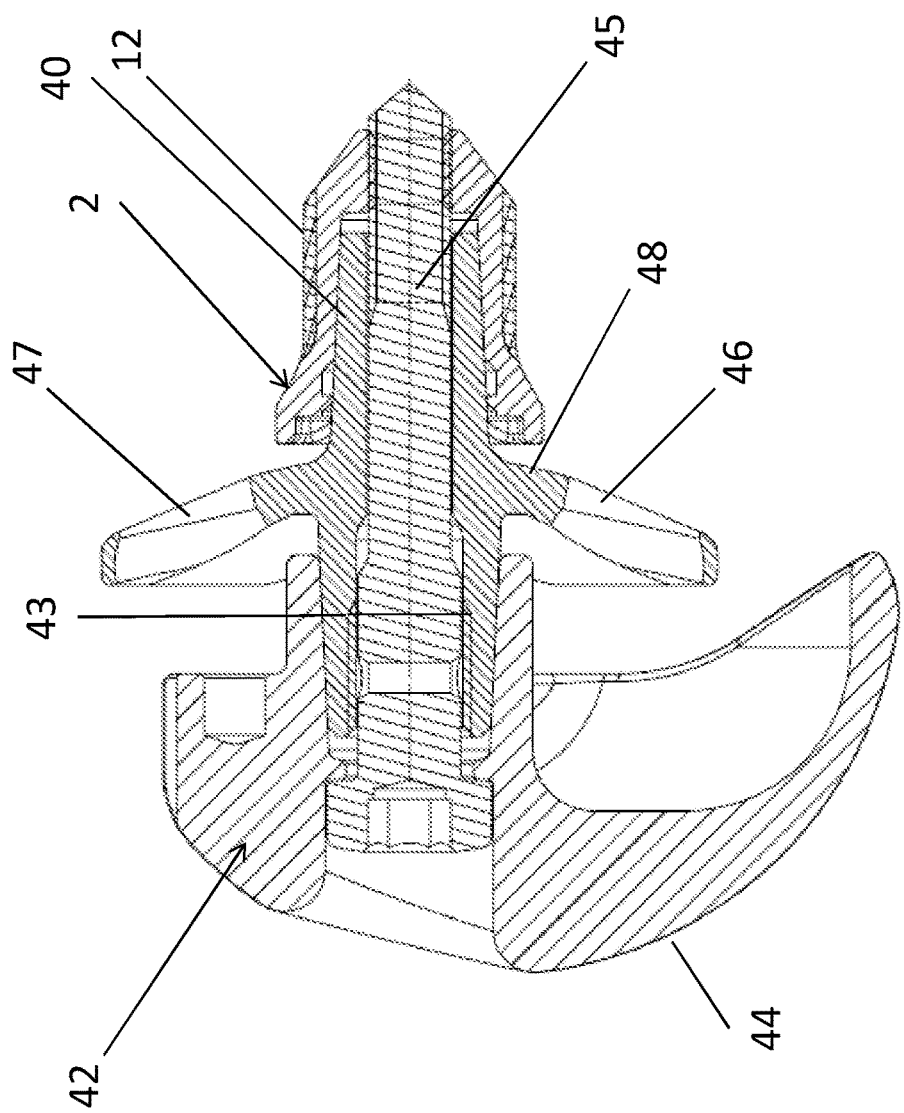
FIG. 12 shows a further schematic partially longitudinally sectioned view of the anchor and the other prosthesis component according to the invention engaged with each other.

In this connection, FIG. 12 shows a prosthesis component 9' useful for converting the prosthesis from an anatomical prosthesis to a reverse prosthesis.

Compared to the preceding example of embodiment of the prosthesis component 9, the component 9' may be made of a biocompatible metallic material.

In this case the component 9' has a lug 40 intended to be inserted inside the conical internal cavity 13 of the pin 2 and a facing portion 41 intended to be engaged with a shoulder-blade component 42 of the reverse prosthesis when the latter has a convex articular surface 44.

A screw 45 is provided for fastening this shoulder-blade component 42, being screwed inside the threaded hole 5 of the pin 2, and has the function of tightening the cones so as to lock the component 44 to the component 9' and finally to the pin 2 itself. The screw 45 has a proximal portion of larger diameter which is received into a corresponding cylindrical cavity 43 of the prosthesis component 9'.

The prosthesis component 9' comprises a plate-shaped portion 48 which has a convexity in its surface facing the insert 40.

On the other hand, this portion 48 has a concavity in its surface facing the other portion 41. The portion 48 is provided with at least two holes 46, 47 situated laterally with respect to the longitudinal axis X-X of the prosthesis component 9' for receiving fixing bone screws 49 which can be seen only in FIG. 16.

The decision to use the prosthesis component 9' may also be taken during the course of a surgical operation.

As a result, it is possible to convert an anatomical prosthesis into a reverse prosthesis, also in the operating theatre, allowing the surgeon to repair the articulation should there be a pathology associated with the rotator cuff, without having to remove the anchoring pin 2 incorporated in the bone.

Advantageously, the assembly consisting of anchor element 1, bearing 2 and humeral and glenoid components of the shoulder prosthesis form a parts kit for the installation of a convertible hybrid prosthesis which may be mounted as an anatomical prosthesis or a reverse prosthesis depending on the operating requirements.

In a preferred embodiment, the prosthesis components will be provided pre-assembled together with the component 9 already snap-engaged in the pin 2 with mechanical interference, basically in the anatomical configuration shown in FIGS. 2 to 9. The prosthesis may be converted during an operation by extracting, using special instruments, the high molecular weight polyethylene (UHMWPE) component 9 so as to allow insertion of the other prosthesis component 9' shown in FIGS. 10 to 14 by means of the conical coupling and locking screw.

The invention claimed is:

1. A glenoid anchor for a shoulder joint prosthesis, of the type intended to be fixed to a glenoid cavity of a shoulder blade,
    wherein the glenoid anchor consists only of a structurally independent pin, with an internally hollow conical sleeve, which has a tapered distal end configured for being directly fixed to the glenoid cavity and an open proximal end configured for being removably attached to a prosthesis component,
    wherein said prosthesis component is a lug of either one of an anatomical prosthesis or a reverse prosthesis,
    wherein said glenoid anchor is configured for removal of said lug in order to convert the anatomical prosthesis to the reverse prosthesis or vice-versa, while keeping the structurally independent pin inside the glenoid cavity,
    wherein an outer surface of the sleeve of said pin has a trabecular structure for favouring osteogenesis and bone integration;
    wherein said pin further comprises:
        an annular recess formed inside an internal cavity of the pin, for receiving by means of snap-engagement an edge of the lug of the prosthesis component;
        at least one pair of oppositely arranged anti-rotation notches at said annular recess for receiving oppositely arranged teeth of the lug.

2. The glenoid anchor according to claim 1, wherein a surface of said internal cavity of the pin and an outer surface of said lug of the prosthesis component are engaged with each other by means of mechanical interference.

3. The glenoid anchor according to claim 2, wherein the surface of the internal cavity of the pin is inclined with respect to the longitudinal axis of said pin at a predefined angle with a reduction in an internal diameter towards the distal end of the pin, while the outer surface of the lug of the prosthesis component is inclined with respect to the same longitudinal axis at an angle smaller than said predefined angle.

4. The glenoid anchor according to claim 1, wherein said lug of said prosthesis component is conical and is inserted inside the internal cavity of said pin with controlled interference when said edge is seated inside said annular recess.

5. The glenoid anchor according to claim 1, further comprising another pair of notches for receiving by means of snap-engagement a second pair of teeth, said another pair of notches being angularly spaced from each other.

6. The glenoid anchor according to claim 1, wherein said edge has a toothed profile for snap-engagement inside the annular recess, and prevents undesired removal thereof.

7. The glenoid anchor according to claim 6, wherein the prosthesis component is structurally independent of said pin.

8. The glenoid anchor according to claim 1, wherein the annular recess is formed at said open proximal end.

9. The glenoid anchor according to claim 1, wherein the annular recess is formed at the distal end of the pin.

10. The glenoid anchor according to claim 1, wherein the distal end of said pin is provided with a threaded through-hole for receiving a securing screw of the shoulder joint prosthesis.

11. The glenoid anchor according to claim 1, wherein the proximal end of the pin defines a flared proximal opening which allows access to the internal cavity.

12. The glenoid anchor according to claim 11, wherein a narrower diameter is provided adjacent to the flared proximal opening, inside the internal cavity of the pin, said narrower diameter defining an edge or internal step for seating, in bearing contact, a surface of said lug of the prosthesis component.

13. The glenoid anchor according to claim 1, wherein said prosthesis component is structurally independent of said pin and is made of a different material.

14. The glenoid anchor according to claim 13, wherein said prosthesis component comprises a portion situated opposite said lug and intended to be engaged with a shoulder-blade component of a reverse prosthesis provided with a convex articular surface.

15. The glenoid anchor according to claim 14, wherein the shoulder-blade component of the reverse prosthesis is associated with said prosthesis component by means of a screw engaging inside a threaded hole formed in the distal end of the pin.

16. The glenoid anchor according to claim 15, wherein said screw has a proximal portion of larger diameter which is screwed into a corresponding cylindrical cavity of the prosthesis component.

* * * * *